(12) United States Patent
Matsumoto et al.

(10) Patent No.: US 8,114,014 B2
(45) Date of Patent: Feb. 14, 2012

(54) CAPSULE MEDICAL APPARATUS AND METHOD OF MANUFACTURING THEREOF

(75) Inventors: Jun Matsumoto, Hino (JP); Hidetake Segawa, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 12/796,954

(22) Filed: Jun. 9, 2010

(65) Prior Publication Data

US 2010/0324367 A1 Dec. 23, 2010

Related U.S. Application Data

(63) Continuation of application No. PCT/JP2009/070426, filed on Dec. 4, 2009.

(30) Foreign Application Priority Data

Dec. 9, 2008 (JP) ................................. 2008-313701

(51) Int. Cl.
*A61B 1/06* (2006.01)

(52) U.S. Cl. ....................................... 600/160

(58) Field of Classification Search .................. 600/109, 600/117, 118, 160; 174/525
See application file for complete search history.

(56) References Cited

U.S. PATENT DOCUMENTS

| | | | | |
|---|---|---|---|---|
| 4,533,787 A | * | 8/1985 | Anderegg et al. ............. | 174/251 |
| 6,940,158 B2 | * | 9/2005 | Haba et al. .................... | 257/686 |
| 2001/0006252 A1 | * | 7/2001 | Kim et al. ..................... | 257/688 |
| 2001/0040793 A1 | * | 11/2001 | Inaba ............................ | 361/749 |
| 2004/0104470 A1 | * | 6/2004 | Bang et al. .................... | 257/724 |
| 2005/0224993 A1 | * | 10/2005 | Manepalli et al. ............ | 257/787 |
| 2006/0008949 A1 | * | 1/2006 | Salta, III ....................... | 438/125 |
| 2006/0149132 A1 | * | 7/2006 | Iddan ............................ | 600/160 |
| 2006/0264709 A1 | * | 11/2006 | Fujimori et al. .............. | 600/130 |
| 2007/0118012 A1 | * | 5/2007 | Gilad ............................ | 600/109 |
| 2008/0312504 A1 | * | 12/2008 | Kimoto ......................... | 600/118 |
| 2009/0062605 A1 | * | 3/2009 | Orihara et al. ................ | 600/109 |

FOREIGN PATENT DOCUMENTS

| | | |
|---|---|---|
| JP | 2005-152043 A | 6/2005 |
| JP | 2005-198965 | 7/2005 |
| JP | 2005-205072 A | 8/2005 |
| JP | 2007-075261 | 3/2007 |

OTHER PUBLICATIONS

International Search Report dated Feb. 2, 2010.

\* cited by examiner

*Primary Examiner* — Philip Smith
(74) *Attorney, Agent, or Firm* — Scully, Scott, Murphy & Presser, P.C.

(57) ABSTRACT

A capsule medical apparatus is provided with a plurality of rigid boards which are connected in line via a flexible board; and molded bodies. The molded bodies are formed in a manner of covering functional components mounted on the respective rigid boards. The molded bodies keep an inter-board interval between the rigid boards by intervening between facing rigid boards. The molded bodies keep an inter-board interval between the rigid boards by intervening between facing rigid boards.

12 Claims, 12 Drawing Sheets

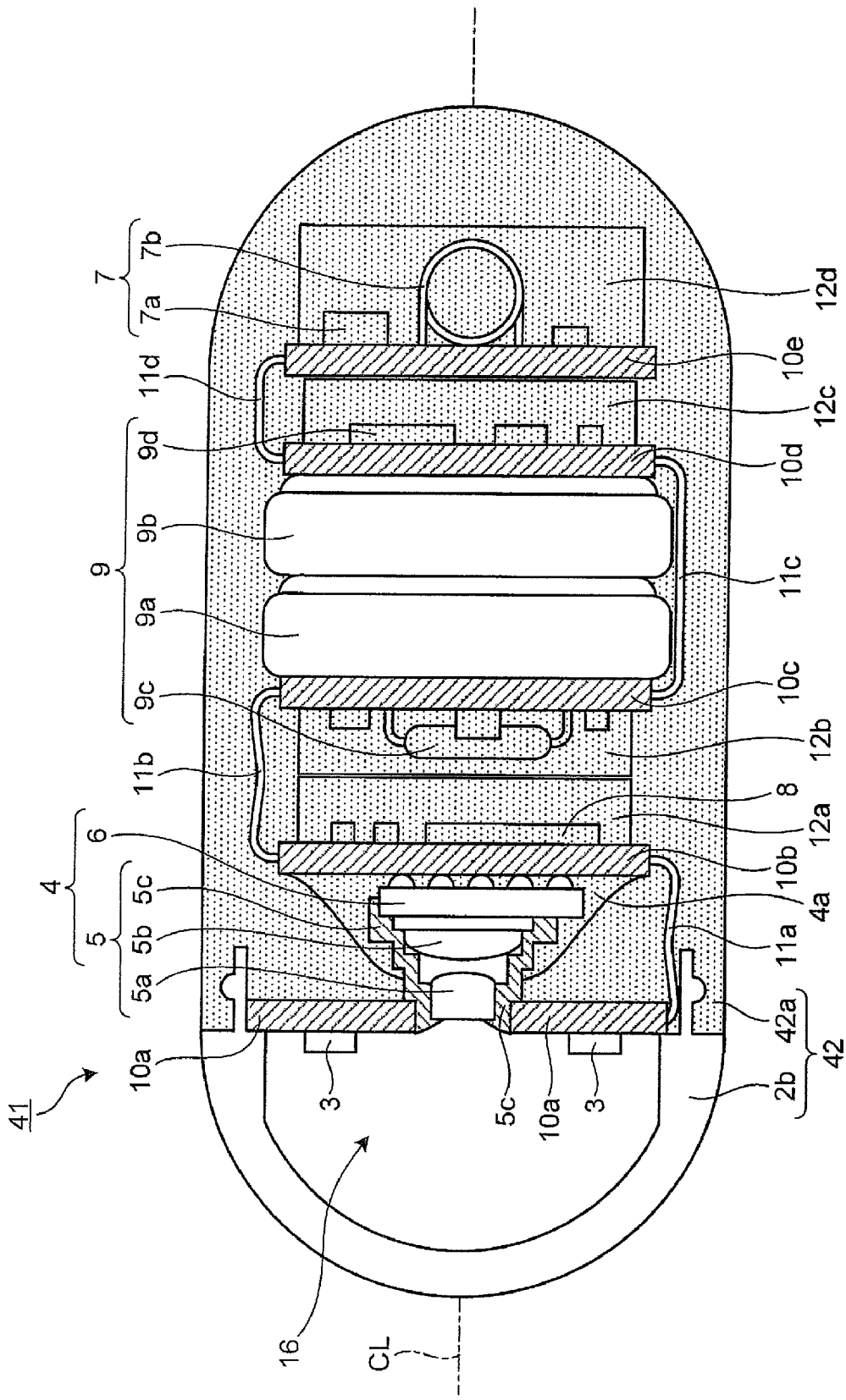

CAPSULE MEDICAL APPARATUS AND METHOD OF MANUFACTURING THEREOF

CROSS-REFERENCE TO RELATED APPLICATIONS

This application is a continuation of PCT international application Ser. No. PCT/JP2009/070426 filed on Dec. 4, 2009 which designates the United States, the entire contents of which are incorporated herein by reference.

BACKGROUND OF THE INVENTION

1. Field of the Invention

The present invention relates to a capsule medical apparatus that is inserted in an inside of organs of a subject like a patient and obtains in-vivo information of the subject; and a method of manufacturing thereof.

2. Description of the Related Art

Conventionally, a capsule medical apparatus which is a swallowable endoscope provided with an imaging function and a wireless communication function inside a capsule-shaped casing has made an appearance in the field of endoscopes. The capsule medical apparatus is inserted, by being swallowed from a mouth and the like, into an inside of organs of a subject like a patient. The capsule medical apparatus inside the subject then captures images of the inside of organs (hereinafter sometimes referred to as "in-vivo images") of the subject while traveling the inside of organs according to the peristaltic movement and the like and wirelessly transmits the obtained in-vivo images to an outside of the subject. The capsule medical apparatus sequentially captures in-vivo images along a time sequence and wirelessly transmits the obtained in-vivo images in an order of the time sequence to the outside of the subject during a period which starts when the capsule medical apparatus is inserted into the inside of the subject and ends when it is naturally excreted to the outside of the subject.

The in-vivo images wirelessly transmitted from the capsule medical apparatus in the time sequence order are sequentially received by a receiver placed outside the subject. The receiver stores a group of in-vivo images received in the time sequence order from the capsule medical apparatus in a recording medium attached thereto in advance. After that, the recording medium storing the group of in-vivo images is detached from the receiver and attached to an image display device. The image display device imports the group of in-vivo images in the attached recording medium and sequentially displays each of the obtained in-vivo images on a display. Users such as a doctor and a nurse can observe each of the in-vivo images displayed in the image display device and observe (examine) the inside of organs of the subject through the observation of the in-vivo images.

Here, this capsule medical apparatus is generally manufactured by sealing, in an inside of a capsule-shaped casing, a combination of a button-shaped battery and a series of circuit boards mounting necessary electronic components such as a solid-state imaging device. Here, the series of circuit boards are realized by linearly connecting a plurality of rigid circuit boards (hereinafter referred to as "rigid board") via a flexible circuit board (hereinafter referred to as "flexible board") having flexibility and various electronic components are mounted on the plurality of the respective rigid boards. The series of circuit boards on which various electronic components are mounted are sealed in the inside of the capsule-shaped casing in such a manner that the plurality of rigid boards are oppositely arranged at predetermined intervals. On the other hand, the button-shaped battery is arranged in the inside of the capsule-shaped casing in such a manner as to be sandwiched between the plurality of rigid boards (see Japanese Patent Application Laid-Open No. 2005-198965).

SUMMARY OF THE INVENTION

According to an aspect of the present invention, a capsule medical apparatus includes a plurality of rigid circuit boards which are connected via a flexible circuit board; and a plurality of molded bodies which are formed in advance in a manner of covering functional components mounted on the plurality of rigid circuit boards, wherein an inter-board interval in the plurality of rigid circuit boards is kept by one of a direct contact between the plurality of molded bodies which are oppositely arranged and a direct contact between the molded body and the rigid circuit board which are oppositely arranged.

According to another aspect of the present invention, a capsule medical apparatus includes a plurality of rigid circuit units which are connected via a flexible circuit board; and a plurality of molded units which are formed in advance in a manner of covering functional components mounted on the plurality of rigid circuit units, wherein an inter-board interval in the plurality of rigid circuit units is kept by one of a direct contact between the plurality of molded units which are oppositely arranged and a direct contact between the molded unit and the rigid circuit unit which are oppositely arranged.

According to still another aspect of the present invention, a method of manufacturing a capsule medical apparatus includes mounting functional components on a plurality of circuit boards; forming molded bodies which cover the functional components on the plurality of circuit boards; and keeping an inter-board interval in the plurality of circuit boards by arranging, after the forming of the molded bodies, the plurality of circuit boards in a manner of facing each other and making the molded bodies intervene between the plurality of circuit boards.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 12 is a cross-sectional view of a configuration example of a capsule medical apparatus according to a fourth embodiment of the present invention.

DETAILED DESCRIPTION OF THE PREFERRED EMBODIMENTS

Exemplary embodiments of a capsule medical apparatus and a method of manufacturing thereof according to the present invention will be explained in detail below with reference to the accompanying drawings. It should be noted that the present invention is not limited to the embodiments.

First Embodiment

Figure 1:
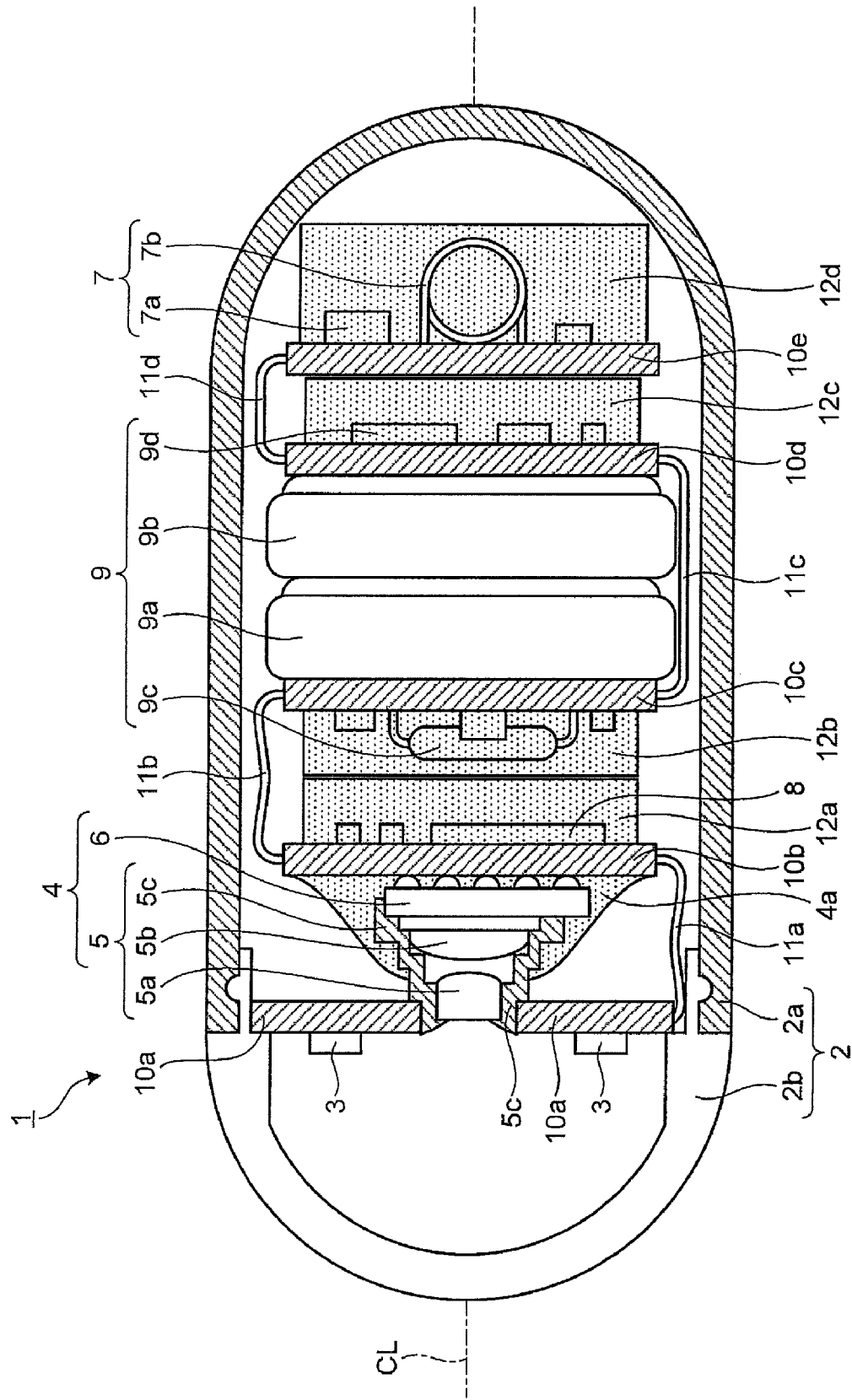
FIG. 1 is a cross-sectional view of a configuration example of a capsule medical apparatus according to a first embodiment of the present invention.

FIG. 1 is a cross-sectional view of a configuration example of a capsule medical apparatus according to a first embodiment of the present invention. As shown in FIG. 1, a capsule medical apparatus 1 according to the first embodiment is provided with a capsule-shaped casing 2 which is realized by a cylindrical casing 2a and a dome-shaped casing 2b; an illumination unit 3 which illuminates an object such as an inside of organs of a subject; an imaging unit 4 which captures images of the object illuminated by the illumination unit 3; a wireless communication unit 7 which wirelessly transmits to outside data of the images captured by the imaging unit 4; an operation controller 8 which controls operations of components of the capsule medical apparatus 1; and a power supply unit 9 which supplies an electric power to the components of the capsule medical apparatus 1. In addition, the capsule medical apparatus 1 is provided with a plurality of rigid boards 10a to 10e which mount functional components such as the imaging unit 4 and the wireless communication unit 7; and flexible boards 11a to 11d which electrically connect the plurality of rigid boards 10a to 10e by intervening in between.

The capsule-shaped casing 2 is formed in a size which allows an insertion to the inside of organs of a subject like a patient and the like, and includes a cylindrical casing 2a one end of which has a dome shape; and a dome-shaped casing 2b which covers the other end (open end) of the cylindrical casing 2a. The dome-shaped casing 2b is a dome-shaped optical member, which is transmissive with respect to an illumination light (a visible light such as a white color light, for example) emitted by the illumination unit 3. On the other hand, the cylindrical casing 2a is a casing having a cylindrical shape and a bottom, which is more or less of an opacity with respect to a visible light. The capsule-shaped casing 2 formed by the cylindrical casing 2a and the dome-shaped casing 2b holds therein, while keeping a water-tightness, functional components (the illumination unit 3, the imaging unit 4, the wireless communication unit 7, the operation controller 8, and the power source unit 9) which are mounted on respective boards of the plurality of rigid boards 10a to 10e connected by the flexible boards 11a to 11d.

The illumination unit 3 is a functional component for illuminating an object of the imaging unit 4. Specifically, the illumination unit 3 is realized by using a light emitting element such as an LED and mounted on the rigid board 10a. The illumination unit 3 emits an illumination light (a visible light of a predetermined wavelength band such as a white color light, for example) with respect to the object of the imaging unit 4 and thereby illuminates, through the dome-shaped casing 2b, the inside of organs of the subject which is the object of the imaging unit 4. Here, the number of the illumination light 3 mounted on the rigid board 10a may be one or more and is not specifically limited to four.

The imaging unit 4 is a functional component for capturing images of the inside of organs of the subject which is the object illuminated by the illumination unit 3, i.e., in-vivo images of the subject. Specifically, the imaging unit 4 is provided with an optical unit 5 such as a lens; and a solid-state imaging device 6 such as a CCD and a CMOS. The imaging unit 4 is mounted on the rigid board 10b, and the solid-state imaging device 6 and a part of the optical unit 5 of the imaging unit 4 are covered by a resin member 4a.

The optical unit 5 is a functional component for condensing a light reflected from the object illuminated by the illumination unit 3 on a light-receiving surface of the solid-state imaging device 6. Specifically, the optical unit 5 is realized by using a plurality of lenses 5a and 5b and a lens frame 5c which holds the lenses 5a and 5b. The lenses 5a and 5b condense a light reflected from the object (the inside of organs of the subject and the like) illuminated by the illumination unit 3 on the light-receiving surface of the solid-state imaging device 6 and form an optical image of the object on the light-receiving surface of the solid-state imaging device 6. The lens frame 5c has a cylindrical structure in which both ends are open and holds the lenses 5a and 5b inside the cylinder. An upper end side of the lens frame 5c is inserted into an opening part formed in the rigid board 10a. On the other hand, a lower end side of the lens frame 5c is fixed to the solid-state imaging device 6. The lens frame 5c in the fixed state makes the lens 5a at the upper end side and the dome-shaped casing 2b face each other and at the same time makes the lens 5b at the lower end side and the light-receiving surface of the solid-state imaging device 6 face each other. Here, it is desirable that an optical axis of the optical unit 5 corresponds to a long axis CL, which is a center axis in a longitudinal direction of the capsule-shaped casing 2.

The solid-state imaging device 6 is a functional component for capturing in-vivo images of the subject. Specifically, the solid-state imaging device 6 is mounted on the rigid board 10b by a bump connection technique and the like. At the light-receiving surface side of the solid-state imaging device 6, the lens frame 5c is fixed as shown in FIG. 1. By receiving a light which is reflected from the object and condensed by the optical unit 5 via the light-receiving surface and performing a photoelectric conversion process on the received light reflected from the subject, the solid-state imaging device 6 captures images of the object, i.e., in-vivo images of the subject illuminated by the illumination unit 3.

The wireless communication unit 7 is a functional component for wirelessly transmitting in-vivo images of the subject captured by the imaging unit 4 to the outside. Specifically, the wireless communication unit 7 is provided with a communication processor 7a which performs communication processes such as a modulation process with respect to an image signal; and an antenna 7b which wirelessly transits the in-vivo images of the subject to the outside. The communication processor 7a and the antenna 7b are mounted on the rigid board 10e. The communication processor 7a obtains an image signal containing data of an in-vivo image of the subject captured by the imaging unit 4 described above from the operation controller 8 and performs communication processes such as a modulation process with respect to the obtained image signal to generate a wireless signal containing the image signal. The communication processor 7a transmits the generated wireless signal to the outside via the antenna 7b based on a control of the operation controller 8. Here, the in-vivo image of the subject wirelessly transmitted by the wireless communication unit 7 is received by a receiver (not shown) arranged outside the subject.

The operation controller 8 is a functional component for controlling operations of the components of the capsule medical apparatus 1. Specifically, the operation controller 8 is realized by using a storage unit which stores a program and the like for realizing functions of the capsule medical apparatus 1, a CPU which executes the stored program in the storage unit, and the like. The operation controller 8 is mounted on a mounting surface which is a reverse side of the imaging unit 4 of the rigid board 10b. The operation controller 8 controls operations of the illumination unit 3, the imaging unit 4, and the wireless communication unit 7 described above and controls input and output of a signal among the components. In this case, the operation controller 8 controls an operation timing of the illumination unit 3 and the solid-state imaging device 6 so that the solid-state imaging device 6 captures an in-vivo image of the subject at a moment when the illumination unit 3 emits the illumination light. Besides, the operation controller 8 obtains a signal on which a photoelectric conversion process is performed by the solid-state imaging device 6 and performs a predetermined signal process with respect to the obtained signal to generate an image signal containing data of the in-vivo image of the subject. Each time an image signal is generated (i.e., each time an in-vivo image is captured by the imaging unit 4), the operation controller 8 controls the communication processor 7a of the wireless communication unit 7 to transmit a wireless signal containing the image signal to the outside.

The power supply unit 9 is a functional component for supplying an electric power to the illumination unit 3, the imaging unit 4, the wireless communication unit 7, and the operation controller 8 described above. Specifically, the power supply unit 9 is provided with batteries 9a and 9b which store a predetermined electric power; a switching unit 9c which switches the electric power supply ON and OFF; and a power source controller 9d which controls a voltage and the like of the supplied electric power. The batteries 9a and 9b are, for example, button type batteries such as a silver oxide battery and arranged between the rigid boards 10c and 10d as shown in FIG. 1. The switching unit 9c is mounted on a mounting surface of the rigid board 10c and switches between ON and OFF states depending on an externally-applied magnetic field, for example. When the switching unit 9c is at ON state, the power source controller 9d arbitrarily supplies electric power of the batteries 9a and 9b to the illumination unit 3, the imaging unit 4, the wireless communication unit 7, and the operation controller 8 while adjusting a voltage to an appropriate value. In contrast, when the switching unit 9c is at OFF state, the power source controller 9d stops supplying the electric power to the components of the capsule medical apparatus 1.

Here, a switching circuit of the power supply unit 9 is not limited to the ON and OFF switching depending on the externally-applied magnetic field and may be an ON and OFF switching based on optical signals such as an infrared light incident from the outside. Besides, the number of batteries of the power supply unit 9 is not specifically limited to two and may be one or more as long as the number falls within a range in which electric power necessary for the components of the capsule medical apparatus 1 can be supplied.

The rigid board 10a, on which functional components such as the illumination unit 3 described above are mounted, is a disk-shaped circuit board on which a circuit for realizing the function of the illumination unit 3 is formed. Besides, the upper end side of the lens frame 5c is inserted into the opening part formed in the rigid board 10a. The rigid board 10b, on which functional components such as the imaging unit 4 and the operation controller 8 described above are mounted, is a disk-shaped circuit board on which a circuit for realizing the functions of the solid-state imaging device 6 and the operation controller 8 is formed.

The rigid board 10c, on which functional components such as the switching unit 9c described above are mounted, is a disk-shaped circuit board on which a circuit for realizing the function of the switching unit 9c is formed. The rigid board 10d, on which functional components such as the power supply controller 9d described above are mounted, is a disk-shaped circuit board on which a circuit for realizing the function of the power source controller 9d is formed. Besides, respective electrode terminals (not shown) which are electrically connected to the batteries 9a and 9b are provided in the rigid boards 10c and 10d. The rigid boards 10c and 10d sandwiches the batteries 9a and 9b in such a manner that the respective electrode terminals are made in contact with the batteries 9a and 9b. The rigid board 10e, on which functional components such as the communication processor 7a and the antenna 7b described above are mounted, is a disk-shaped circuit board on which a circuit for realizing the function of the wireless communication unit 7.

Here, the flexible board 11a electrically connects the rigid boards 10a and 10b and the flexible board 11b electrically connects the rigid boards 10b and 10c. In addition, the flexible board 11c electrically connects the rigid boards 10c and 10d and the flexible board 11d electrically connects the rigid boards 10d and 10e. The plurality of rigid boards 10a to 10e described above are connected in line by the plurality of flexible boards 11a to 11d and arranged in such a manner as to face each other as shown in FIG. 1 by folding the flexible circuit board parts. In this case, the rigid board 10b faces each of the rigid boards 10a and 10c, and the rigid board 10d faces each of the rigid boards 10c and 10e. The plurality of rigid boards 10a to 10e are arranged in the inside of the capsule-shaped casing 2 in this mutually facing manner.

Meanwhile, molded bodies 12a to 12d in a manner of covering functional components are respectively formed on component mounting surfaces of the rigid boards 10b to 10e among the plurality of rigid boards 10a to 10e described above. The plurality of molded bodies 12a to 12d intervene between facing boards among the plurality of rigid boards 10b to 10e and keep respective inter-board intervals of the rigid boards 10b to 10e.

Specifically, the molded bodies 12a to 12d are formed of a resin which can be formed into a desired cubic shape by a given molding technique, and sustain a cubic structure like a cylinder, a rectangular cylinder, or the like which is capable of a surface joining between upper end surfaces at a temperature equal to or lower than an ambient temperature under which the capsule medical apparatus 1 is operable. The molded body 12a is formed in a manner of covering functional components such as the operation controller 8 by a molding process using a mold tool which is designed in accordance with a component mounting surface of the rigid board 10b, and arranged on the component mounting surface of the rigid board 10b. The molded body 12b is formed in a manner of covering functional components such as the switching unit 9c by a molding process using a mold tool which is designed in accordance with a component mounting surface of the rigid board 10c, and arranged on the component mounting surface of the rigid board 10c. The molded body 12c is formed in a manner of covering functional components such as the power source controller 9d by a molding process using a mold tool which is designed in accordance with a component mounting surface of the rigid board 10d, and arranged on the component mounting surface of the rigid board 10d. The molded body 12d is formed in a manner of covering functional components such as the wireless communication unit 7 by a molding process using a mold tool which is designed in accordance with a component mounting surface of the rigid board 10e, and arranged on the component mounting surface of the rigid board 10e.

Here, the molded bodies 12a and 12b intervene between the rigid boards 10b and 10c which face each other among the plurality of rigid boards 10a to 10e. The molded bodies 12a and 12b are subject to a surface jointing with each other in a state where the rigid boards 10b and 10c are oppositely arranged and thereby keep an inter-board interval of the rigid boards 10b and 10c. In this case, each of the mutually-facing surfaces of the molded bodies 12a and 12b is, for example, formed into a planar state. In addition, the molded body 12c intervenes between the rigid boards 10d and 10e which face each other among the plurality of rigid boards 10a to 10e. The molded body 12c is subject to a surface jointing with the rigid board 10e in a state where the rigid boards 10d and 10e are oppositely arranged and thereby keeps an inter-board interval of the rigid boards 10d and 10e. In this case, a surface of the molded body 12c facing the rigid board 10e is, for example, formed into a planar state in accordance with the surface of the rigid board 10e. Besides, the molded body 12d intervenes between the rigid board 10e and an inner wall of the capsule-shaped casing 2 (specifically, an inner wall of the cylindrical casing 2a). In this case, the molded body 12d is pressed onto the inner wall of the cylindrical casing 2a and thereby keeps an interval between the rigid board 10e and the inner wall of the cylindrical casing 2a.

Here, while a filling resin which realizes the molded bodies 12a to 12d may be a thermoplastic resin or a thermosetting resin, it is desirable that the resin is a hot melt resin which can be formed by a molding technique with comparatively low pressure. When the molded bodies 12a to 12d are formed of the a hot melt resin, a pressure to be applied on functional components of each of the rigid boards 10b to 10e at the time of the molding process can be made as low as possible and thereby a stress on the functional components can be reduced. Furthermore, the molded bodies 12a to 12d can be solidified in comparatively short time, as a result of which a shorter amount of time in manufacturing the capsule medical apparatus 1 can be promoted.

Figure 2:
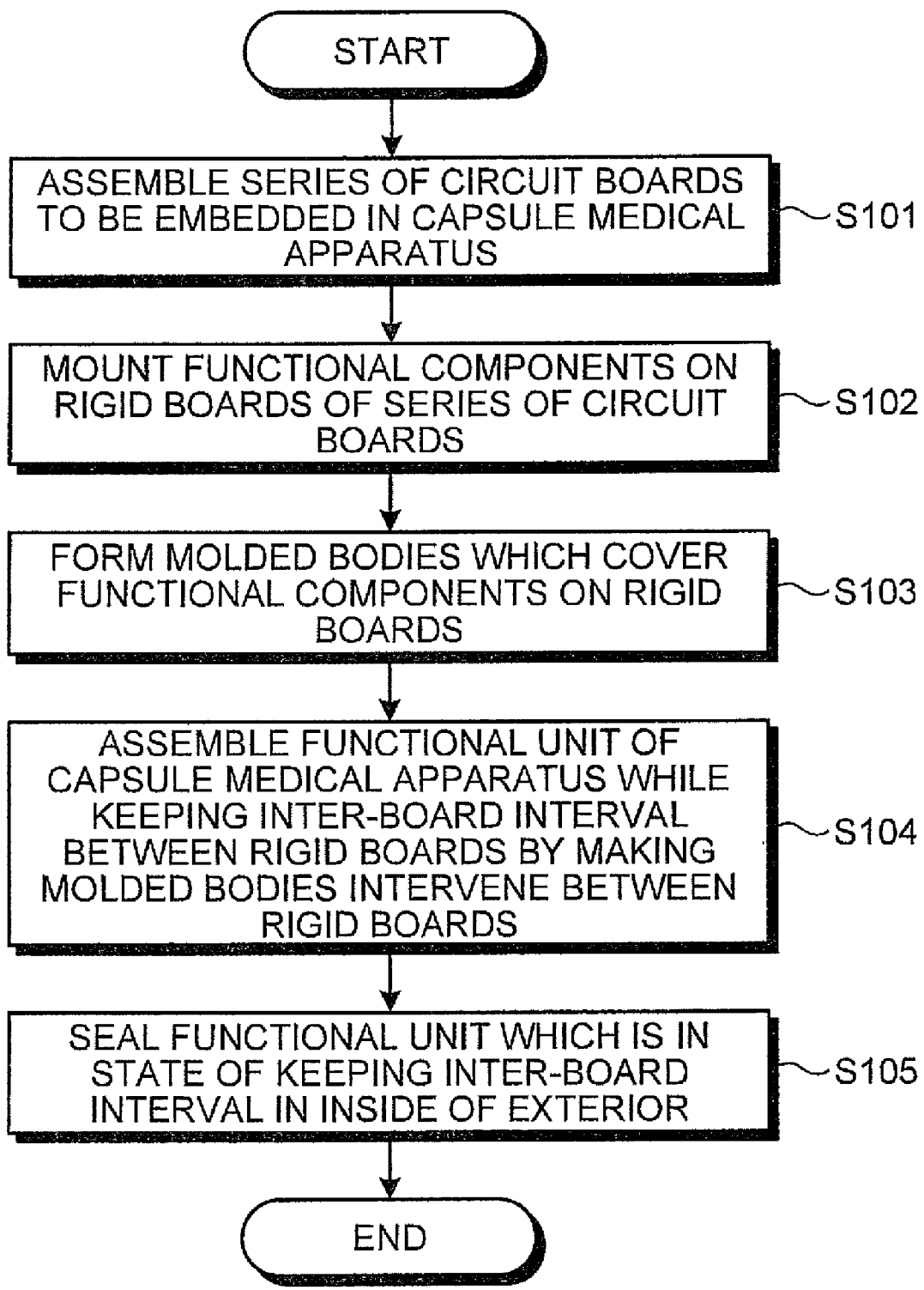
FIG. 2 is a flowchart exemplifying a method of manufacturing the capsule medical apparatus according to the first embodiment of the present invention.
Figure 3:
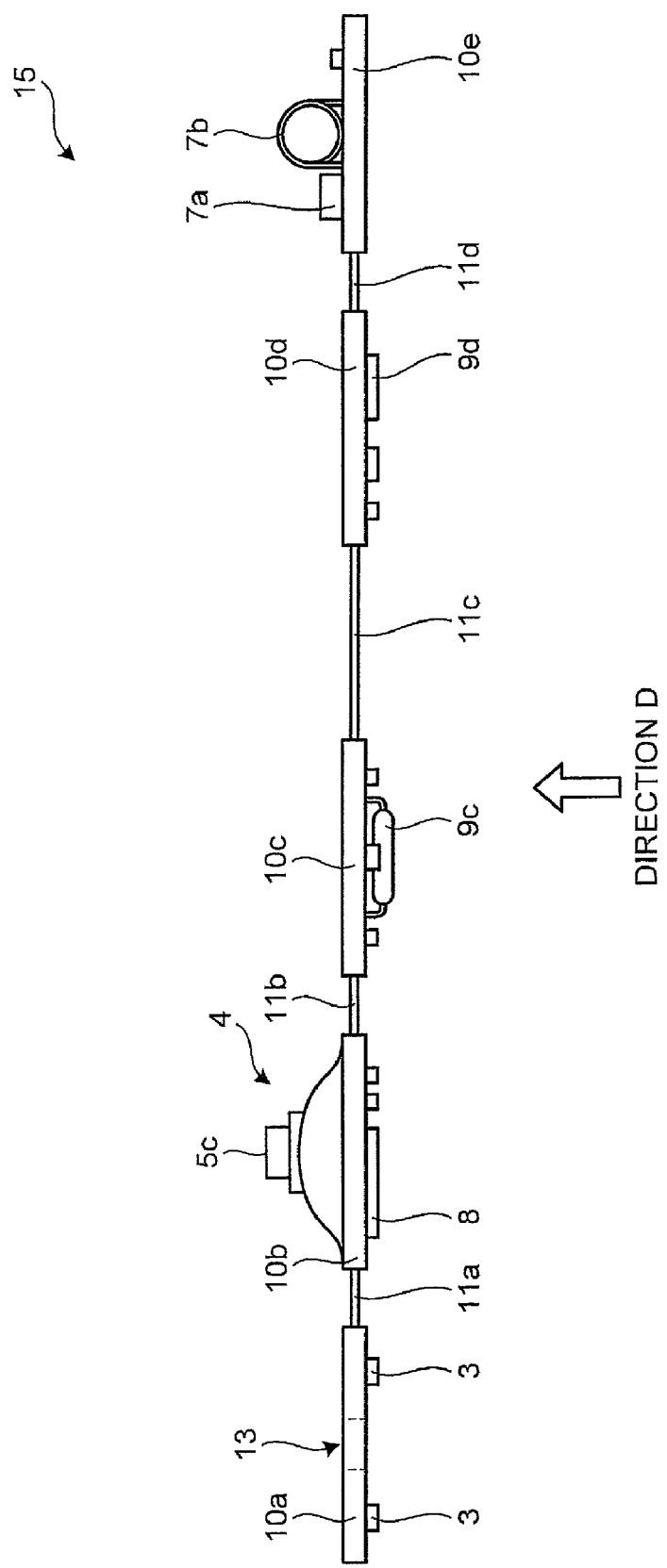
FIG. 3 is a view exemplifying a series of circuit boards to be embedded in the capsule medical apparatus according to the first embodiment of the present invention.
Figure 4:
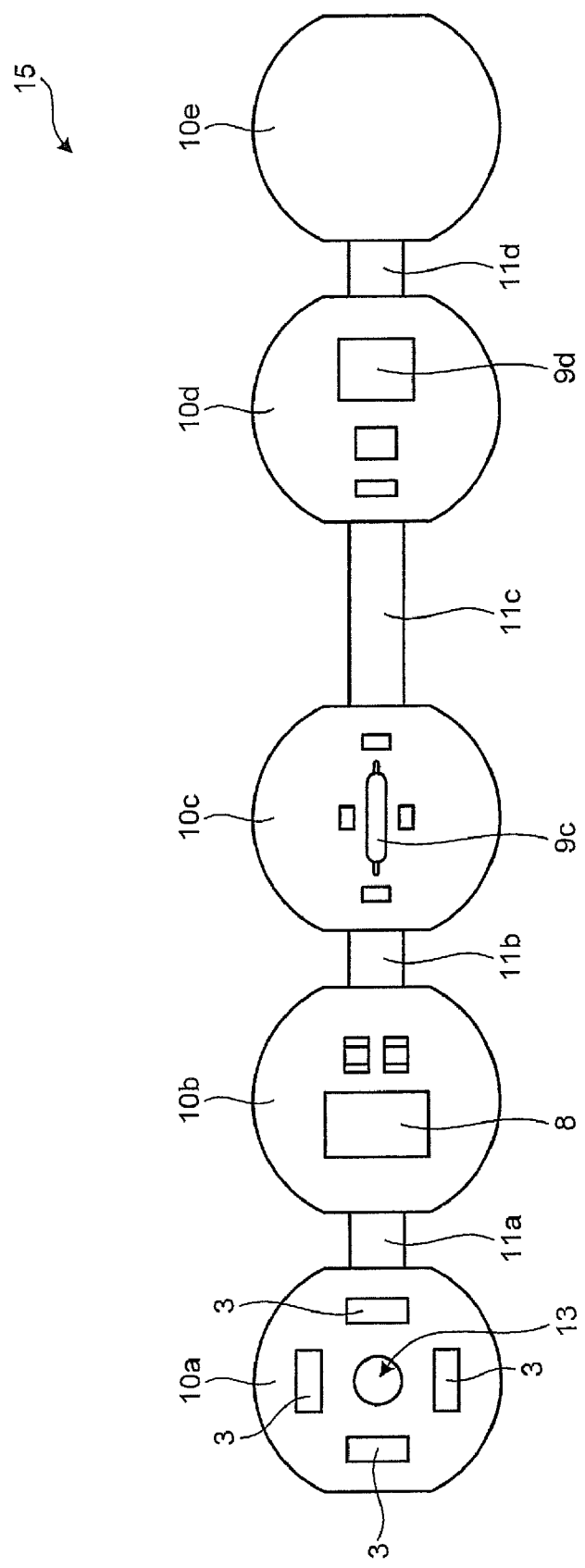
FIG. 4 is a view exemplifying the series of circuit boards seen from the direction D in FIG. 3.
Figure 5:
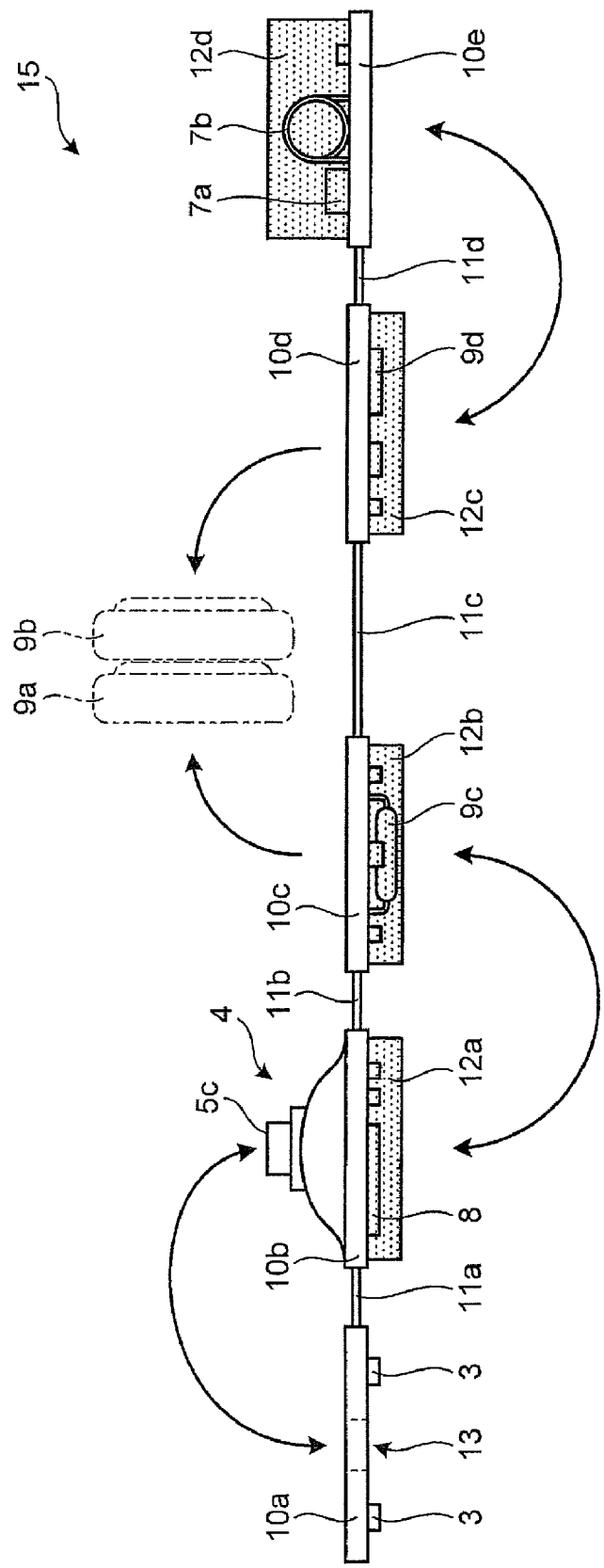
FIG. 5 is a view exemplifying the series of circuit boards in a state where molded bodies which cover functional components on rigid boards are formed.
Figure 6:
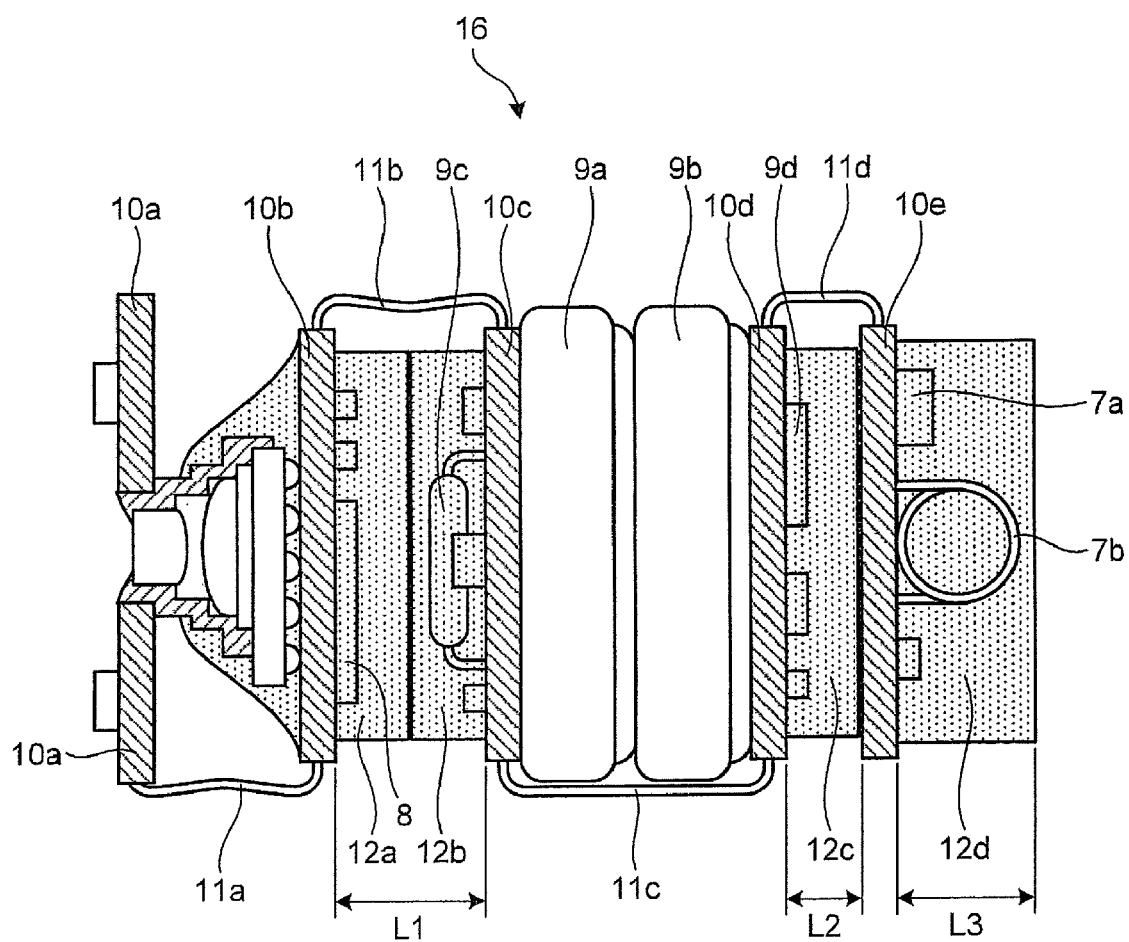
FIG. 6 is a view exemplifying a functional unit to be embedded in the capsule medical apparatus according to the first embodiment of the present invention.
Figure 7:
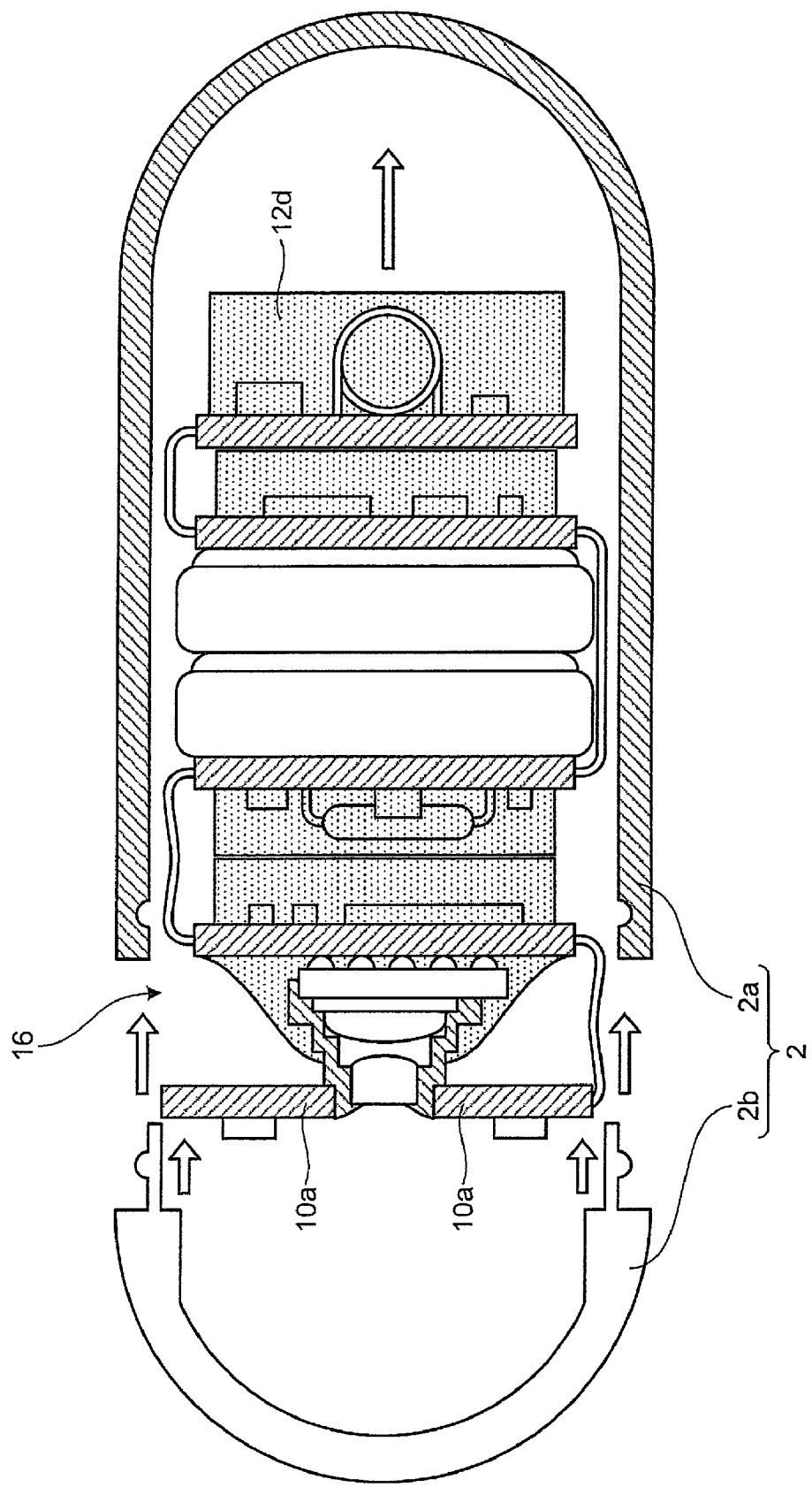
FIG. 7 is a view of a state where the functional unit is sealed in an inside of a capsule-shaped casing.

Next, a method of manufacturing the capsule medical apparatus 1 according to the first embodiment of the present invention will be explained. FIG. 2 is a flowchart exemplifying a method of manufacturing the capsule medical apparatus according to the first embodiment of the present invention. FIG. 3 is a view exemplifying the series of circuit boards to be embedded in the capsule medical apparatus according to the first embodiment of the present invention. FIG. 4 is a view exemplifying the series of circuit boards seen from the direction D in FIG. 3. FIG. 5 is a view exemplifying the series of circuit boards in a state where molded bodies which respectively cover functional components on rigid boards are formed. FIG. 6 is a view exemplifying a functional unit to be embedded in the capsule medical apparatus according to the first embodiment of the present invention. FIG. 7 is a view of a state where the functional unit is sealed in the inside of the capsule-shaped casing.

As shown in FIG. 2, the series of circuit boards to be embedded in the capsule medical apparatus 1 is first assembled (step S101). Specifically, a series of circuit boards 15 as shown in FIG. 3 is assembled by connecting the plurality of rigid boards 10a to 10e described above in line via the flexible boards 11a to 11d at step S101. In the series of circuit boards 15, the rigid boards 10b is electrically connected to the rigid board 10a via the flexible board 11a and to the rigid board 10c via the flexible board 11b. In addition, the rigid board 10d is electrically connected to the rigid board 10c via the flexible board 11c and to the rigid board 10e via the flexible board 11d.

Next, functional components are mounted on the plurality of circuit boards included in the series of circuit boards 15 assembled at step S101 (step S102). Specifically, functional components such as the illumination unit 3 are mounted on a mounting surface of the rigid board 10a, functional components such as the imaging unit 4 and the operation controller 8 are mounted on respective mounting surfaces of the rigid board 10b among the plurality of rigid circuit boards 10a to 10e at step S102 as shown in FIGS. 3 and 4. In addition, functional components such as the switching unit 9c are mounted on a mounting surface of the rigid board 10c, functional components such as the power supply controller 9d are mounted on a mounting surface of the rigid board 10d, functional components such as the communication processor 7a and the antenna 7b are mounted on a mounting surface of the rigid board 10e. In this case, the illumination unit 3, the operation controller 8, the switching unit 9c, and the power source controller 9d are mounted on the mounting surfaces at the same side in the series of circuit boards 15. By contrast, the imaging unit 4 is mounted on the mounting surface at a reverse side of the operation controller 8 of the mounting surfaces at both sides of the rigid board 10b. In addition, the communication processor 7a and the antenna 7b are mounted on the mounting surface at a reverse side of the power supply controller 9d of the rigid board 10e. Here, an opening part 13 for inserting the lens frame 5c of the imaging unit 4 mounted on the rigid board 10b is formed in advance in the rigid board 10a on which the illumination unit 3 is mounted.

After that, molded bodies which cover the mounted various functional components are arbitrarily formed on the plurality of circuit boards on which the various functional components are mounted at step S102 (step S103). Specifically, on the mounting surface at the side of the operation controller 8 of the rigid board 10b among the plurality of rigid circuit boards 10a to 10e described above, a molding tool designed in accordance with this mounting surface is placed and a filling resin such as a hot melt resin is poured into the molding tool to form the molded body 12a on this molding surface at step S103, as shown in FIG. 5. In this case, the molded body 12a is formed in a manner of covering functional components such as the operation controller 8 via a molding process using the molding tool and sustains a cubic structure like a cylinder, a rectangular cylinder, or the like which is capable of a surface joining between upper end surfaces. In addition, on the mounting surface of the rigid board 10c, a molding tool designed in accordance with this mounting surface is placed and a filling resin such as a hot melt resin is poured into the molding tool to form the molded body 12b on this mounting surface. In this case, the molded body 12b is formed in a manner of covering functional components such as the switching unit 9c via a molding process using the molding tool and sustains the same cubic structure as the molded body 12*a* described above. In addition, on the mounting surface of the rigid board 10*d*, a molding tool designed in accordance with this mounting surface is placed and a filling resin such as a hot melt resin is poured into the molding tool to form the molded body 12*c* on this mounting surface. In this case, the molded body 12*c* is formed in a manner of covering functional components such as the power source controller 9*d* via a molding process using the molding tool and sustains the same cubic structure as the molded body 12*a* described above. In addition, on the mounting surface of the rigid board 10*e*, a molding tool designed in accordance with this mounting surface is placed and a filling resin such as a hot melt resin is poured into the molding tool to form the molded body 12*d* on this mounting surface. In this case, the molded body 12*d* is formed in a manner of covering functional components such as the communication processor 7*a* and the antenna 7*b* via a molding process using the molding tool and sustains the same cubic structure as the molded body 12*a* described above.

Next, by making the molded bodies on respective circuit boards intervene in interspaces of the plurality of circuit boards arranged in a manner of facing each other after the molded bodies are formed as described above, each inter-board interval of the plurality of circuit boards is kept. In other words, while keeping each inter-board interval of the rigid boards 10*b* to 10*e* with the molded bodies 12*a* to 12*c* intervening between rigid boards of the series of circuit board 15 described above, the functional unit of the capsule medical apparatus is assembled (step S104).

Specifically, the flexible board 11*b* is folded to a direction of making an upper end surface of the molded body 12*a* and an upper end surface of the molded body 12*b* face, the rigid boards 10*b* and 10*c* are oppositely arranged, and then the upper end surface of the molded body 12*a* and the upper end surface of the molded body 12*b* are joined at step S104 as shown in FIG. 5. As a result, the molded bodies 12*a* and 12*b* keep the inter-board interval between the rigid boards 10*b* and 10*c* by intervening between the rigid boards 10*b* and 10*c* in the oppositely arranged state. Besides, the flexible board 11*d* is folded to a direction of making an upper end surface of the molded body 12*c* and a back surface (a board surface at the reverse side of the component mounting surface) of the rigid board 10*e* face, the rigid boards 10*d* and 10*e* are oppositely arranged, and then the upper end surface of the molded body 12*c* and the back surface of the rigid board 10*e* are joined. As a result, the molded body 12*c* keeps the inter-board interval between the rigid boards 10*d* and 10*e* by intervening between the rigid boards 10*d* and 10*e* in the oppositely arranged state.

Here, the surface joining between the molded bodies 12*a* and 12*b* described above can be realized by fixing each other on respective upper end surfaces (facing surfaces) of the molded bodies 12*a* and 12*b* by using an adhesive agent, an adhesive tape, or the like. Besides, when the molded bodies 12*a* and 12*b* are formed of a hot melt resin, the surface joining of the molded bodies 12*a* and 12*b* may be realized by performing a heating treatment and a solidifying treatment (a cooling treatment) on the molded bodies 12*a* and 12*b* mutually in the state of the surface joining on the upper end surfaces. The surface joining between the molded body 12*c* and the rigid board 10*e* described above can be realized by fixing each other on the upper end surface of the molded body 12*c* and the back surface of the rigid board 10*e* by using an adhesive agent, an adhesive tape, or the like.

In contrast, as for the rigid board 10*a*, the flexible board 11*a* is folded to a direction of making a back surface of the rigid board 10*a* and the side of the imaging unit 4 of the rigid board 10*b* face, and the rigid boards 10*a* and 10*b* are oppositely arranged. Then, the lens frame 5*c* of the imaging unit 4 is inserted into the opening part 13 of the rigid board 10*a* to assemble the rigid board 10*a* to the imaging unit 4. By this, the inter-board interval between the rigid boards 10*a* and 10*b* is kept. Here, the lens frame 5*c* of the imaging unit 4 may be fixedly fitted into the opening part 13 of the rigid board 10*a* based on a tolerance or may be fixed in the opening part 13 of the rigid board 10*a* by an adhesive agent.

The batteries 9*a* and 9*b* are assembled to the series of circuit boards 15 in such a manner as to be sandwiched between the rigid boards 10*c* and 10*d* described above. In this case, the flexible board 11*c* is folded to a direction of making the back surface of the rigid board 10*c* and the back surface of the rigid board 10*d* face, the rigid boards 10*c* and 10*d* are oppositely arranged, and then the batteries 9*a* and 9*b* are sandwiched between the rigid boards 10*c* and 10*d* in the oppositely arranged state, as shown in FIG. 5. As a result, the battery 9*a* has a contact with the electrode terminal on the back surface of the rigid board 10*c* and the battery 9*b* has a contact with the electrode terminal on the back surface of the rigid board 10*d*. Here, though not shown specifically, the sandwiched state of the batteries 9*a* and 9*b* between the rigid boards 10*c* and 10*d* may be maintained by putting a heat shrink tube on the rigid boards 10*c* and 10*d* which are in the state of sandwiching the batteries 9*a* and 9*b* therebetween and making this heat shrinkable tube shrink.

The functional unit 16 shown in FIG. 6 is assembled by fitting the series of circuit boards 15 and the batteries 9*a* and 9*b* together in such a way as described at step S104. The functional unit 16 is a unit for realizing the function of the capsule medical apparatus 1. In the functional unit 16, the plurality of rigid boards 10*a* to 10*e* are arranged in a manner of facing each other in the state of being connected in line by the flexible boards 11*a* to 11*d* as shown in FIG. 6. Among the inter-board intervals of the rigid boards 10*a* to 10*e* in the oppositely arranged state, the batteries 9*a* and 9*b* are sandwiched between the rigid boards 10*c* and 10*d*, the molded bodies 12*a* and 12*b* intervene between the rigid boards 10*b* and 10*c*, and the molded body 12*c* intervenes between the rigid boards 10*d* and 10*e*. Besides, the molded body 12*d* is arranged at a rear end part of the functional unit 16, i.e., on a component mounting surface of the rigid board 10*e*.

After step S104 described above is completed, the functional unit 16 which is in the state of maintaining the inter-board intervals of the rigid boards 10*a* to 10*e* as shown in FIG. 6 is sealed inside the capsule-shaped casing 2, which is an outer covering of the capsule medical apparatus 1 (step S105), so that manufacturing of the capsule medical apparatus 1 is completed.

Specifically, at step S105 as shown in FIG. 7, the functional unit 16 in the state of maintaining the inter-board intervals is housed in the inside of the cylindrical casing 2*a* which is a body part of the capsule-shaped casing 2, then the dome-shaped casing 2*b* is fitted to the open end of the cylindrical casing 2*a*, and thereby the open end of the cylindrical casing 2*a* is blocked while keeping a water-tightness therein. In this case, the molded body 12*d* of the functional unit 16 is pressed to the inner wall (inner wall of the dome-shaped part) on the bottom part of the cylindrical casing 2*a*. In addition, an end part of the dome-shaped casing 2*b* is pressed to a marginal part of the rigid board 10*a* of the functional unit 16. In this manner, the functional unit 16 is sealed and positioned in the inside of the capsule-shaped casing 2 in the state of maintaining intervals of the rigid boards.

Here, the molded bodies 12*a* and 12*b* intervening between the rigid boards 10*b* and 10*c* in the functional unit 16 are solid substances of a cubic structure which hold therein the functional components of the rigid boards 10*b* and 10*c* as shown in FIG. 6. Between the rigid boards 10b and 10c, the molded bodies 12a and 12b keep an inter-board interval L1 which is enough to secure a space for arranging the functional components such as the operation controller 8 and the switching unit 9c mounted on the rigid boards 10b and 10c. In addition, the molded body 12c intervening the rigid boards 10d and 10e in the functional unit 16 is a solid substance of a cubic structure which holds therein the functional components of the rigid board 10d as shown in FIG. 6. Between the rigid boards 10d and 10e, the molded body 12c keeps an inter-board interval L2 which is enough to secure a space for arranging the functional components such as the power source controller 9d mounted on the rigid board 10d.

Besides, the molded body 12d which is arranged at the rear end part of the functional unit 16, i.e., on the component mounting surface of the rigid board 10e is a solid substance of a cubic structure which holds therein the functional components of the rigid board 10e as shown in FIG. 6. Between the rigid board 10e and the inner wall of the cylindrical casing 2a, the molded body 12d keeps an inter-board interval L3 which is enough to secure a space for arranging the functional components such as the communication processor 7a and the antenna 7b mounted on the rigid board 10e.

As described so far, the first embodiment is configured such that molded bodies covering functional components on the plurality of rigid boards connected by flexible boards in line are formed and made to intervene between facing rigid boards among the plurality of rigid boards to keep inter-board intervals of the plurality of rigid boards. Therefore, inter-board intervals of the plurality of rigid boards on which various functional components are mounted can be kept easily by making a surface joining between molded bodies which face each other or between a molded body and a rigid board which face each other, without providing a filling between rigid boards while adjusting intervals of rigid boards in the conventional way. Thus, a capsule medical apparatus can be manufactured easily in a short amount of time while securing inter-board intervals necessary for arranging functional components in the plurality of rigid boards.

Moreover, the surface joining between facing molded bodies or between facing molded body and rigid board can be realized easily in a short amount of time by using a hot melt resin for the molded bodies, as a result of which a shorter amount of time in manufacturing a capsule medical apparatus can be promoted and a capsule medical apparatus can be manufactured more easily.

Second Embodiment

Next, a second embodiment of the present invention will be explained. While a molded body in a manner of covering functional components is formed on a rigid board in the first embodiment described above, air bubbles are additionally formed in an inside of the molded body in the second embodiment.

Figure 8:
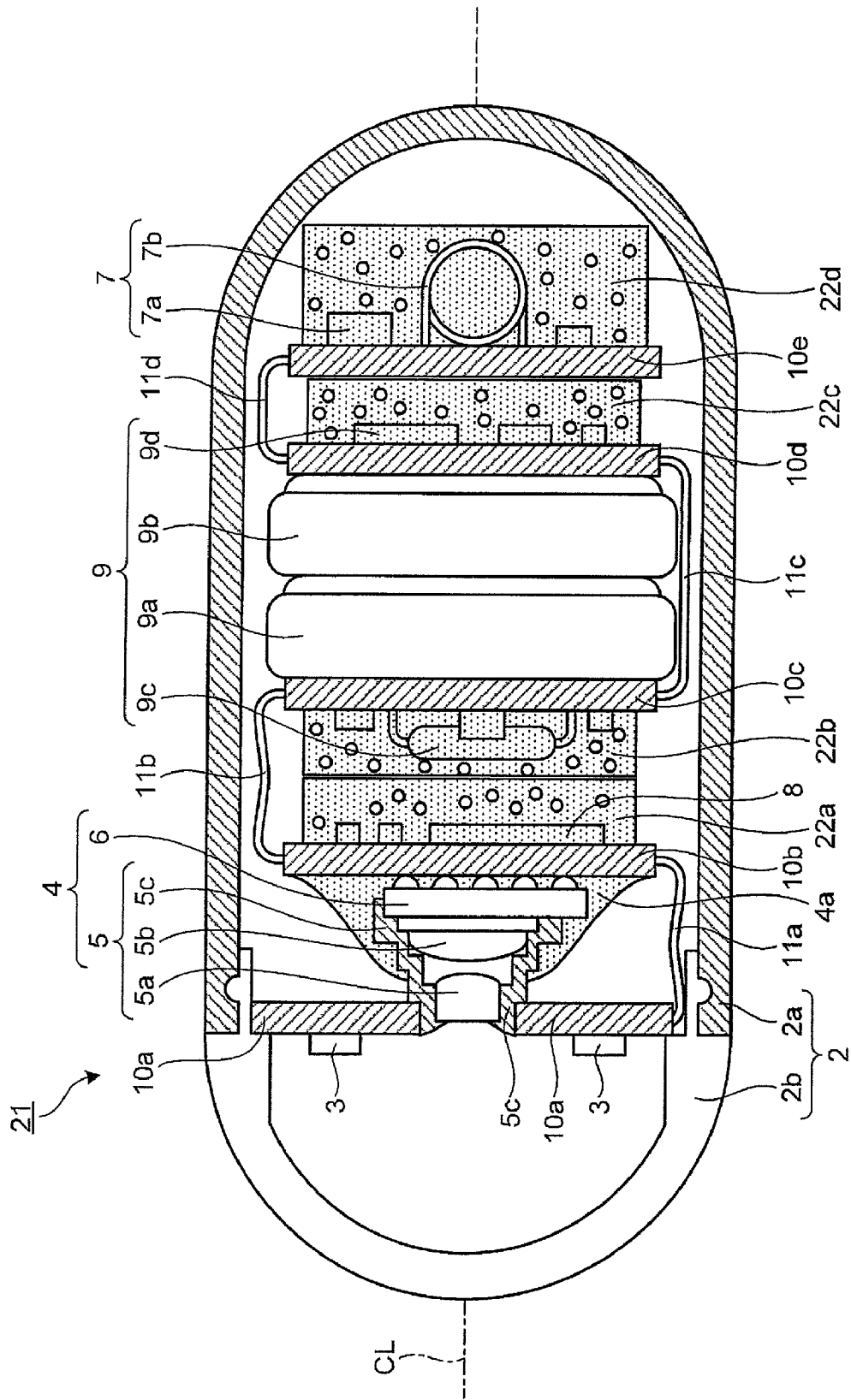
FIG. 8 is a cross-sectional view of a configuration example of a capsule medical apparatus according to a second embodiment of the present invention.

FIG. 8 is a cross-sectional view of a configuration example of a capsule medical apparatus according to a second embodiment of the present invention. As shown in FIG. 8, a capsule medical apparatus 21 according to the second embodiment is provided with molded bodies 22a to 22d including air bubbles in place of the molded bodies 12a to 12d in the capsule medical apparatus 1 according to the first embodiment described above. Other constituents are in common with the first embodiment and the common constituents are provided with common reference characters.

Each of the molded bodies 22a to 22d includes a lot of minute air bubbles and holds therein functional components on a rigid board as shown in FIG. 8. The molded body 22a, which covers the functional components on the rigid board 10b in place of the molded body 12a in the first embodiment, is reduced in weight compared to the molded body 12a by including a lot of minute air bubbles therein. The molded body 22b, which covers the functional components on the rigid board 10c in place of the molded body 12b in the first embodiment, is reduced in weight compared to the molded body 12b by including a lot of minute air bubbles therein. The molded body 22c, which covers the functional components on the rigid board 10d in place of the molded body 12c in the first embodiment, is reduced in weight compared to the molded body 12c by including a lot of minute air bubbles therein. The molded body 22d, which covers the functional components on the rigid board 10e in place of the molded body 12d in the first embodiment, is reduced in weight compared to the molded body 12d by including a lot of minute air bubbles therein. Except for the inclusion of the air bubbles, the molded bodies 22a to 22d have the same configuration and function as the molded bodies 12a to 12d in the first embodiment.

The capsule medical apparatus 21 with this configuration can be manufactured in a method roughly similar to the method of manufacturing the capsule medical apparatus 1 according to the first embodiment. In other words, the capsule medical apparatus 21 according to the second embodiment is manufactured in the method roughly similar to steps S101 to S105 shown in FIG. 2. In this case, step S103 in the manufacturing method of the capsule medical apparatus 21 is different from that in the first embodiment.

Specifically at step S103 in the second embodiment, on the mounting surface at the side of the operation controller 8 of the rigid board 10b, a molding tool designed in accordance with this mounting surface is placed and a filling resin such as a hot melt resin is poured with air bubbles into the molding tool to form the molded body 22a on this mounting surface. In this case, the molded body 22a is formed, similarly to the molded body 12a in the first embodiment, in a manner of covering the functional components such as the operation controller 8, includes minute air bubbles therein, and sustains a cubic structure like a cylinder, a rectangular cylinder, or the like which is capable of a surface joining between upper end surfaces. In addition, on the mounting surface of the rigid board 10c, a molding tool designed in accordance with this mounting surface is placed and a filling resin such as a hot melt resin is poured with air bubbles into the molding tool to form the molded body 22b on this mounting surface. In this case, the molded body 22b is formed, similarly to the molded body 12b in the first embodiment, in a manner of covering the functional components such as the switching unit 9c, includes minute air bubbles therein, and sustains the same cubic structure as the molded body 22a described above. In addition, on the mounting surface of the rigid board 10d, a molding tool designed in accordance with this mounting surface is placed and a filling resin such as a hot melt resin is poured with air bubbles into the molding tool to form the molded body 22c on this mounting surface. In this case, the molded body 22c is formed, similarly to the molded body 12c in the first embodiment, in a manner of covering the functional components such as the power source controller 9d, includes minute air bubbles therein, and sustains the same cubic structure as the molded body 22a described above. In addition, on the mounting surface of the rigid board 10e, a molding tool designed in accordance with this mounting surface is placed and a filling resin such as a hot melt resin is poured with air bubbles into the molding tool to form the molded body 22d on this mounting surface. In this case, the molded body 22d is formed, similarly to the molded body 12*d* in the first embodiment, in a manner of covering the functional components such as the communication processor 7*a* and the antenna 7*b*, includes minute air bubbles therein, and sustains the same cubic structure as the molded body 22*a* described above.

Here, the molded bodies 22*a* to 22*d* described above may be formed by pouring a filling resin with a glass balloon which is a hollow minute glass ball into a molding tool, instead of pouring a filling resin with air bubbles into a molding tool at step S103 in the second embodiment. In this case, the molded bodies 22*a* to 22*d* include therein a lot of glass balls therein and thereby can include a lot of minute air bubbles.

As described so far, the second embodiment is configured such that molded bodies covering functional components and include a lot of minute air bubbles are formed on the plurality of rigid boards connected by flexible boards in line and are made to intervene between facing rigid boards among the plurality of rigid boards to keep inter-board intervals of the plurality of rigid boards, similarly to the first embodiment. Therefore, while keeping the same advantages as the case in the first embodiment, a molded body on a rigid board can be reduced in weight and thereby a lighter capsule medical apparatus can be manufactured easily in a short amount of time.

According to the second embodiment, a density of a capsule medical apparatus can be lowered without increasing a volume of a capsule medical apparatus, as a result of which a capsule medical apparatus which can float in a liquid for example can be manufactured easily in a short amount of time.

Third Embodiment

Next, a third embodiment of the present invention will be explained. While facing molded bodies or facing molded body and rigid board are joined on surfaces by an adhesive agent and the like in the first embodiment described above, facing rigid boards or facing molded body and rigid board are joined on surfaces by a snap fastening in the third embodiment.

Figure 9:
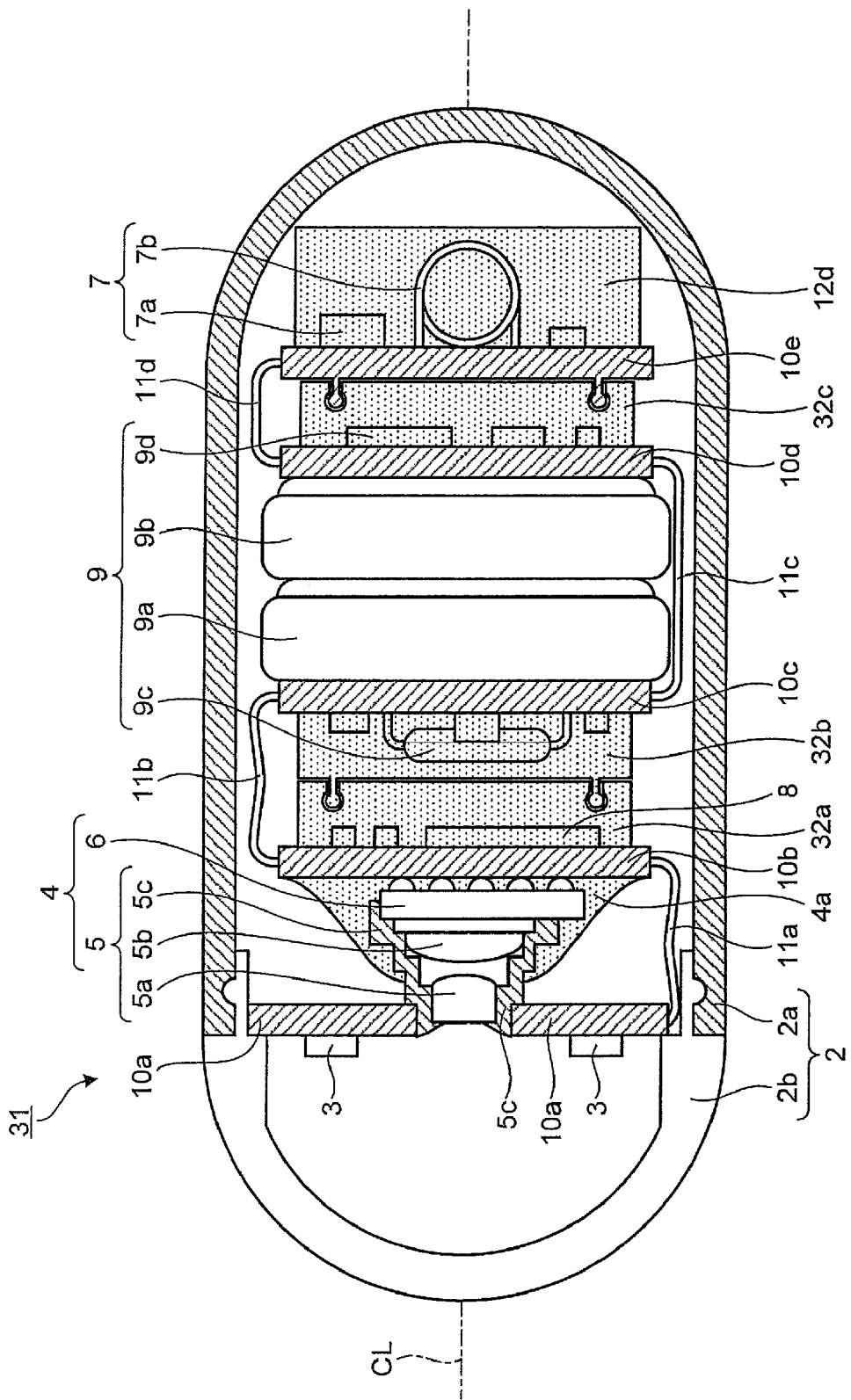
FIG. 9 is a cross-sectional view of a configuration example of a capsule medical apparatus according to a third embodiment of the present invention.

FIG. 9 is a cross-sectional view of a configuration example of a capsule medical apparatus according to the third embodiment of the present invention. As shown in FIG. 9, a capsule medical apparatus 31 according to the third embodiment is provided with molded bodies 32*a* to 32*c* which can be fastened with snaps in place of the molded bodies 12*a* to 12*c* in the capsule medical apparatus 1 according to the first embodiment described above. Besides, the rigid board 10*e* is provided with a protruding part which enables a snap-fastening of the molded body 32*c* on a back surface side in the third embodiment. Other constituents are in common with the first embodiment and the common constituents are provided with common reference characters.

Figure 10:
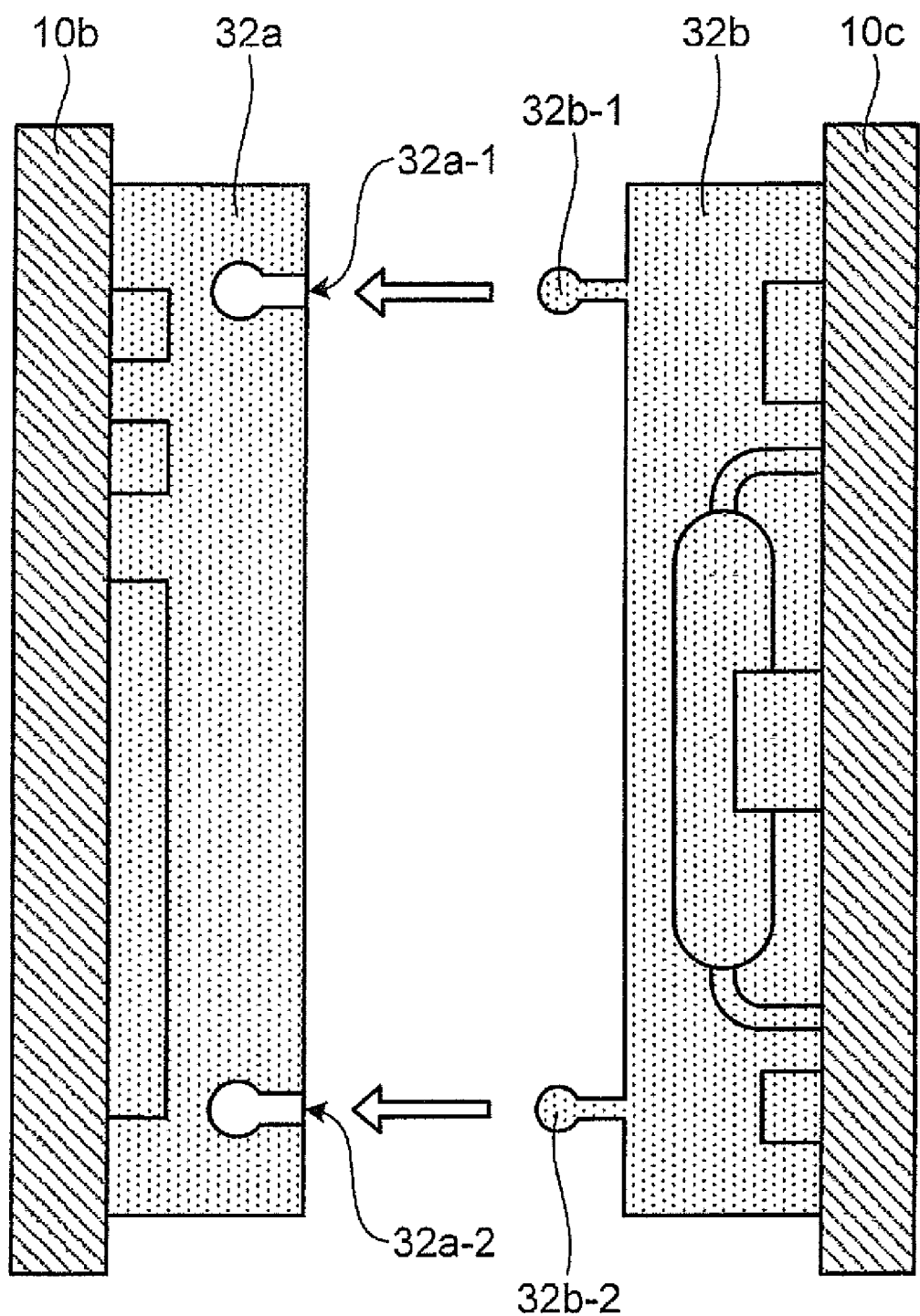
FIG. 10 is a view exemplifying a structure for fastening facing molded bodies with snaps.
Figure 11:
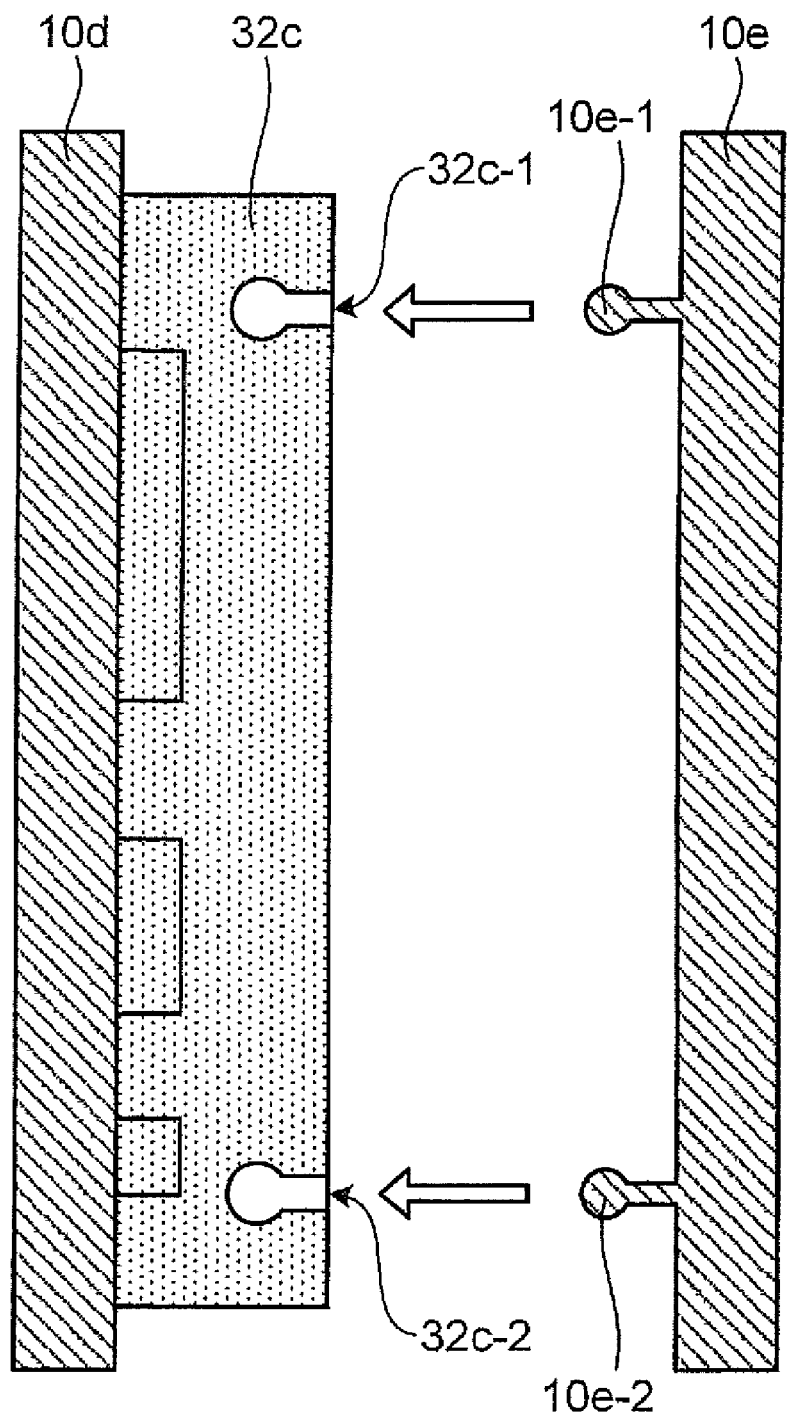
FIG. 11 is a view exemplifying a structure for fastening, with snaps, a molded body and a rigid board which face each other.

The molded bodies 32*a* to 32*c* have a snap-fastening structure which enables fastening facing molded bodies or facing molded body and rigid board with snaps. FIG. 10 is a view exemplifying a structure for fastening facing molded bodies with snaps. FIG. 11 is a view exemplifying a structure for fastening, with snaps, a molded body and a rigid board which face each other. The molded body 32*a* covers the functional components on the rigid board 10*b* in place of the molded body 12*a* in the first embodiment. At an upper end surface side of the molded body 32*a*, snap-fastening parts 32*a*-1 and 32*a*-2 having a hole shape are formed as shown in FIG. 10. The molded body 32*b* covers the functional components on the rigid board 10*c* in place of the molded body 12*b* in the first embodiment. At an upper end surface side of the molded body 32*b*, snap-fastening parts 32*b*-1 and 32*b*-2 having a protruding shape are formed as shown in FIG. 10. The molded bodies 32*a* and 32*b* are fastened with each other by respectively making the snap-fastening parts 32*b*-1 and 32*b*-2 having the protruding shape fit the snap-fastening parts 32*a*-1 and 32*a*-2 having the hole shape. In contrast, the molded body 32*c* covers the functional components on the rigid board 10*d* in place of the molded body 12*c* in the first embodiment. At an upper end surface side of the molded body 32*c*, snap-fastening parts 32*c*-1 and 32*c*-2 having a hole shape are formed as shown in FIG. 11. The molded body 32*c* is fastened to the rigid board 10*e* by respectively making the snap-fastening parts 10*e*-1 and 10*e*-2 having the protruding shape which are formed on the facing rigid board 10*e* fit the snap-fastening parts 32*c*-1 and 32*c*-2 having the hole shape. Here, except for the provision of the snap-fastening structure, the molded bodies 32*a* to 32*c* have the same configuration and function as the molded bodies 12*a* to 12*c* in the first embodiment.

The capsule medical apparatus 31 with this configuration can be manufactured in a method roughly similar to the method of manufacturing the capsule medical apparatus 1 according to the first embodiment. In other words, the capsule medical apparatus 31 according to the third embodiment is manufactured in the method roughly similar to steps S101 to S105 shown in FIG. 2. In this case, step S104 in the manufacturing method of the capsule medical apparatus 31 is different from that in the first embodiment only in a method of a surface joining between facing molded bodies or between facing molded body and rigid board.

Specifically, the flexible board 11*b* is folded to a direction of making an upper end surface of the molded body 32*a* and an upper end surface of the molded body 32*b* face, the rigid boards 10*b* and 10*c* are oppositely arranged, and then the upper end surface of the molded body 32*a* and the upper end surface of the molded body 32*b* are joined with snaps at step S104 in the third embodiment. In this case, the snap-fastening parts 32*b*-1 and 32*b*-2 of the molded body 32*b* are made to fit the snap-fastening parts 32*a*-1 and 32*a*-2 of the molded body 32*a* respectively and thereby the molded bodies 32*a* and 32*b* are fastened as shown in FIG. 10. As a result, the molded bodies 32*a* and 32*b* keep the inter-board interval between the rigid boards 10*b* and 10*c* by intervening between the rigid boards 10*b* and 10*c* in the oppositely arranged state, similarly to the case in the first embodiment. Besides, the flexible board 11*d* is folded to a direction of making an upper end surface of the molded body 32*c* and a back surface of the rigid board 10*e* face, the rigid boards 10*d* and 10*e* are oppositely arranged, and then the upper end surface of the molded body 32*c* and the back surface of the rigid board 10*e* are joined with snaps. In this case, the snap-fastening parts 10*e*-1 and 10*e*-2 of the rigid board 10*e* are made to fit the snap-fastening parts 32*c*-1 and 32*c*-2 of the molded body 32*c* respectively and thereby the molded body 32*c* and the rigid board 10*e* are fastened as shown in FIG. 11. As a result, the molded body 32*c* keeps the inter-board interval between the rigid boards 10*d* and 10*e* by intervening between the rigid boards 10*d* and 10*e* in the oppositely arranged state, similarly to the case in the first embodiment.

As described so far, the third embodiment is configured such that molded bodies having a snap-fastening structure are formed on the plurality of rigid boards connected by flexible boards in line, facing molded bodies or facing molded body and rigid board are joined on surfaces with snaps in oppositely arranging the plurality of rigid boards, and other constituents are configured similarly to the first embodiment. Therefore, while keeping the same advantages as the case in the first embodiment described above, a surface joining between facing molded bodies or between facing molded body and rigid board can be realized easily without using an adhesive agent and the like, as a result of which a capsule medical apparatus can be manufactured more easily in a shorter amount of time.

Fourth Embodiment

Next, a fourth embodiment of the present invention will be explained. While the functional unit 16 is housed in the inside of the cylindrical casing 2a which is a cylindrical casing with a bottom in the first embodiment described above, the functional unit 16 is configured to be embedded in an inside of a body casing which is formed of a filling resin such as a hot melt resin in the fourth embodiment.

FIG. 12 is a cross-sectional view of a configuration example of a capsule medical apparatus according to the fourth embodiment of the present invention. As shown in FIG. 12, a capsule medical apparatus 41 according to the fourth embodiment is provided with a capsule-shaped casing 42 in place of the capsule-shaped casing 2 in the capsule medical apparatus 1 according to the first embodiment described above. The capsule-shaped casing 42 is provided with a body casing 42a formed of a filling resin in place of the cylindrical casing 2a in the first embodiment described above. Other constituents are in common with the first embodiment and the common constituents are provided with common reference characters.

Except for the provision of the body casing 42a in place of the cylindrical casing 2a described above, the capsule-shaped casing 42 has the same configuration and function as the capsule-shaped casing 2 in the first embodiment. The body casing 42a, which is an exterior body formed in a manner of embedding at least the rigid boards 10a to 10e, has the same outer shape as the cylindrical casing 2a described above. The body casing 42a is formed into a tablet shape via a molding process using a molding tool which is designed in accordance with the functional unit 16 including the plurality of rigid boards 10a to 10e on which various functional components are mounted and the like, and covers nearly the entirety of the functional unit 16. Here, while a filling resin which realizes the body casing 42a may be a thermoplastic resin or a thermosetting resin, it is desirable that the resin is a hot melt resin which can be formed by a molding technique with comparatively low pressure. When the body casing 42a is formed of the hot melt resin, a pressure to be applied on the functional unit 16 at the time of the molding process can be made as low as possible and thereby a stress on the functional components in the functional unit 16 can be reduced. Furthermore, the body casing 42a can be solidified in comparatively short time, as a result of which a shorter amount of time in manufacturing the capsule medical apparatus 41 can be promoted.

The capsule medical apparatus 41 with this configuration can be manufactured in a method roughly similar to the method of manufacturing the capsule medical apparatus 1 according to the first embodiment. In other words, the capsule medical apparatus 41 according to the fourth embodiment is manufactured in the method roughly similar to steps S101 to S105 shown in FIG. 2. In this case, step S105 in the manufacturing method of the capsule medical apparatus 41 is different from that in the first embodiment.

Specifically, the functional unit 16 (see FIG. 6) of the capsule medial apparatus 41 is placed in a predetermined molding tool and a filling resin such as a hot melt resin is poured into this molding tool at step S105 in the fourth embodiment. By this, a molded casing which covers at least one part of the functional unit 16, for example, the body casing 42a in a manner of embedding nearly the entirety of the functional unit 16 as shown in FIG. 12 is formed. In this case, the functional unit 16 except for the component mounting surface of the rigid board 10a is embedded in the inside of the body casing 42a which is molded via the molding process.

Then, an end part of the dome-shaped casing 2b is pressed into an end part of the body casing 42a which is in the state where the functional unit 16 is embedded therein to fix the dome-shaped casing 2b to the body casing 42a. By this, the capsule-shaped casing 42 as an outer covering of the capsule medial apparatus 41 is realized and the functional unit 16 is sealed in the inside of the capsule-shaped casing 42.

At step S105 in the fourth embodiment, the end part of the dome-shaped casing 2b and the functional unit 16 may be embedded in the inside of the body casing 42a by making in advance the end part of the dome-shaped casing 2b in a state of being pressed to the marginal part of the rigid board 10a. In this case, the functional unit 16 which is in the state where the end part of the dome-shaped casing 2b is pressed to the marginal part of the rigid board 10a is placed in a predetermined molding tool, a filling resin such as a hot melt resin is poured into the molding tool, and thereby the body casing 42a in the manner of embedding the end part of the dome-shaped casing 2b and nearly the entirety of the functional unit 16 is formed.

As described so far, the fourth embodiment of the present invention is configured such that while a filling resin is formed into a body casing shape which is a body of the capsule-shaped casing via a molding process, nearly the entirety of the functional unit including the plurality of rigid boards on which functional components are mounted and the like is embedded in the inside of the body casing formed of the filling resin, and other constituents are configured similarly to the first embodiment. Therefore, while keeping the same advantages as the case in the first embodiment, the functional unit can be easily sealed in the inside of the capsule medical apparatus, as a result of which a capsule medical apparatus can be manufactured more easily in a shorter amount of time.

Here, while a clearance between the cylindrical casing 2a and the functional unit 16 is left at the time of housing the functional unit 16 in the cylindrical casing 2a of the capsule-shaped casing 2 in the first to third embodiments, the present invention is not limited thereto and the position of the functional unit 16 in the inside of the capsule-shaped casing 2 may be fixed by providing a filler such as an adhesive agent in the clearance between the cylindrical casing 2a and the functional unit 16. Alternatively, the functional unit 16 may be housed in the cylindrical casing 2a in a gas atmosphere such as a helium gas which is lighter than the air or in a vacuum and thereby the clearance between the cylindrical casing 2a and the functional unit 16 ma be filled with a gas such as a helium gas lighter than the air. By this, a weight of a capsule medical apparatus can further be saved.

Besides, while the body casing 42a which is filled by a filling resin such as a hot melt resin is formed in the fourth embodiment described above, the present invention is not limited thereto and a filling resin may be poured into a molding tool with air bubbles or glass balloons to form a body casing including therein a lot of minute air bubbles. By this, a weight of a capsule medical apparatus can further be saved.

Moreover, while a capsule medical apparatus of a monocular type having therein a single imaging unit is exemplified in the first to fourth embodiments described above, the present invention is not limited thereto and the capsule medical apparatus according to the present invention may be a capsule medical apparatus of a compound-eye type having therein a plurality of imaging units.

Besides, while a capsule medical apparatus which includes therein an imaging function and obtains in-vivo images as an example of in-vivo information is exemplified in the first to fourth embodiments, the present invention is not limited thereto and may be a capsule medical apparatus which measures pH information inside a living body as in-vivo information; a capsule medical apparatus which is provided with a function of spreading or injecting a medication inside a living body; or a capsule medical apparatus which obtains, as in-vivo information, substances (body tissues and the like) inside a living body. In this case, a capsule-shaped casing which serves as an outer covering of a capsule medical apparatus may not be provided with a dome-shaped casing which is transmissive with respect to a visible light such as a white color light and may totally be formed of a filling resin such as a hot melt resin, for example.

Furthermore, a capsule medical apparatus according to the present invention is not limited to the embodiments specifically described above, and may be in any arbitrary forms realized in combination of the first to fourth embodiments described above. For example, it may be a capsule medical apparatus capable of a snap-fastening between the molded bodies $22a$ and $22b$ and between the molded body $22c$ and the rigid board $10e$, by adding the snap-fastening structure similar to the case in the third embodiment to the molded bodies $22a$ to $22c$ including therein a lot of minute air bubbles as described (a capsule medical apparatus realized by combining the second and the third embodiments). Alternatively, it may be a capsule medical apparatus which has a structure in which molded bodies including therein a lot of minute air bubbles similarly to the case in the second embodiment are embedded in the inside of the body casing $42a$ (a capsule medical apparatus realized by combining the second and the fourth embodiments), a capsule medical apparatus which has a structure in which molded bodies provided with a snap-fastening part similarly to the case in the third embodiment are embedded in the inside of the body casing $42a$ (a capsule medical apparatus realized by combining the third and the fourth embodiments), or a capsule medical apparatus realized by combining these structures (a capsule medical apparatus realized by combining the second to fourth embodiments).

As described above, the capsule medical apparatus and the method of manufacturing thereof according to the present invention are useful respectively for an observation of an inside of a subject and for manufacturing the apparatus used for the observation, and are especially suitable as a capsule medical apparatus which can easily keep inter-board intervals of a plurality of circuit boards on which various functional components are mounted and can be manufactured easily in a short amount of time; and a method of manufacturing thereof.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule medical apparatus, comprising:
   a plurality of rigid circuit boards which are connected via a flexible circuit board; and
   a plurality of molded bodies which are formed in a manner of covering functional components mounted on the plurality of rigid circuit boards before the plurality of rigid circuit boards are oppositely arranged,
   wherein the plurality of molded bodies keep an inter-board interval in the plurality of rigid circuit boards by a surface joining between the plurality of molded bodies which are oppositely arranged or a surface joining between the oppositely-arranged molded body and the rigid board,
   wherein the plurality of rigid circuit boards include:
   a first board on which a light emitting element is mounted,
   a second board on which an imaging unit is mounted, one of the plurality of molded bodies being formed on a reverse side of the imaging unit,
   a third board and a fourth board for controlling power supply, one of the plurality of molded bodies being formed on a side of the third board to be faced with the molded body of the second board, one of the plurality of molded bodies being formed on a side of the fourth board not to be faced with the molded body of the third board, and
   a fifth board on which an antenna for wireless communications is mounted on a side not to be faced with the molded body of the fourth board, one of the plurality of molded bodies being formed in a manner of covering the antenna,
   wherein the molded bodies of the second board and the third board keep an inter-board interval by a surface joining therebetween, the molded body of the fourth board keeps an inter-board interval by a surface joining between the molded body of the fourth board and the fifth board, and the first board and the molded body of the fifth board are pressed onto an inner wall of a casing of the capsule medical apparatus.

2. The capsule medical apparatus according to claim 1, wherein, in arranging the plurality of rigid circuit boards in a manner of facing each other, a surface of one molded body which faces oppositely-arranged other one of the molded body and the rigid circuit board is formed into a planar state.

3. The capsule medical apparatus according to claim 1, wherein the plurality of molded bodies are formed of a hot melt resin.

4. The capsule medical apparatus according to claim 1, wherein the plurality of molded bodies include therein air bubbles.

5. The capsule medical apparatus according to claim 1, wherein the plurality of molded bodies include a snap-fastening part which enables oppositely-arranged molded bodies to be fastened with a snap.

6. The capsule medical apparatus according to claim 1, comprising a capsule-shaped casing having a body part which is formed in a manner of embedding at least the plurality of rigid circuit boards.

7. The capsule medical apparatus according to claim 1, wherein the surface joining between the molded bodies of the second board and the third board includes heating treatment and solidifying treatment between the molded bodies in a state where the molded bodies are in contact with each other.

8. A method of manufacturing a capsule medical apparatus, comprising:
   mounting functional components on a plurality of circuit boards;
   forming molded bodies which cover the functional components on the plurality of circuit boards; and
   keeping an inter-board interval in the plurality of circuit boards by arranging, after the forming of the molded bodies, the plurality of circuit boards in a manner of facing each other and making the molded bodies intervene between the plurality of circuit boards by a surface joining between the oppositely-arranged molded bodies or a surface joining between the oppositely-arranged molded body and the rigid board, wherein the mounting includes mounting a light emitting element on a first board and mounting an imaging unit on a second board, the forming includes forming one of the molded bodies on a reverse side of the imaging unit, forming one of the molded bodies on a side of a third board to be faced with the molded body of the second board, and forming one of the molded bodies on a side of a fourth board not to be faced with the molded body of the third board, the third board and the fourth board being for controlling power supply, the mounting includes mounting an antenna for wireless communication on a fifth board on a side not to be faced with the molded body of the fourth board, the forming includes forming one of the molded bodies in a manner of covering the antenna, the keeping includes keeping an inter-board interval in the molded bodies of the second board and the third board by a surface joining therebetween and keeping an inter-board interval in the molded body of the fourth board by a surface joining between the molded body of the fourth board and the filth board, and the first board and the molded body of the fifth board are pressed onto an inner wall of a casing of the capsule medical apparatus.

9. The method of manufacturing a capsule medical apparatus according to claim 8, wherein the forming of the molded bodies includes pouring a hot melt resin into a molding tool which is placed on a surface for mounting the functional components of the plurality of circuit boards.

10. The method of manufacturing a capsule medical apparatus according to claim 8, wherein the keeping of the inter-board interval includes making one of a surface joining between the molded bodies and a surface joining between any one of the plurality of circuit boards and the molded body.

11. The method of manufacturing a capsule medical apparatus according to claim 9, wherein the keeping of the inter-board interval includes making a surface joining via a heating treatment between the molded bodies in a state where the molded bodies formed of the hot melt resin are in contact with each other on surfaces.

12. The method of manufacturing a capsule medical apparatus according to claim 8, further comprising forming a molded casing which is at least a part of a casing including therein the plurality of circuit boards of a capsule medical apparatus and in which at least a part of the plurality of circuit boards keeping the inter-board interval in the keeping of the inter-board interval is embedded.

* * * * *